(12) United States Patent
Fritts et al.

(10) Patent No.: US 8,235,058 B1
(45) Date of Patent: Aug. 7, 2012

(54) FOOT CALLOUS REMOVAL DEVICE

(76) Inventors: Nellie J. Fritts, Cincinnati, OH (US);
Carl Lee Helton, Cincinnati, OH (US)

(*) Notice: Subject to any disclaimer, the term of this patent is extended or adjusted under 35 U.S.C. 154(b) by 17 days.

(21) Appl. No.: 13/007,760

(22) Filed: Jan. 17, 2011

(51) Int. Cl.
*A45D 29/18* (2006.01)
*A45D 29/04* (2006.01)

(52) U.S. Cl. ............... 132/76.4; 132/73.5; 132/75.6

(58) Field of Classification Search ............ 132/746.4, 132/75.6, 73.5, 73, 75.3; 36/138; 223/113
See application file for complete search history.

(56) References Cited

U.S. PATENT DOCUMENTS

| | | | |
|---|---|---|---|
| 258,154 A * | 5/1882 | Thomson | ............. 36/1 |
| 954,061 A * | 4/1910 | Von Taxis | ............. 223/113 |
| 2,676,597 A | 4/1954 | Colbert | |
| 5,621,986 A * | 4/1997 | Medina et al. | ............. 36/136 |
| 5,974,701 A * | 11/1999 | Busch | ............. 36/138 |
| 5,996,163 A | 12/1999 | Galizia | |
| 6,325,069 B1 | 12/2001 | Heims | |
| 7,219,387 B1 | 5/2007 | Moore | |
| 2005/0103356 A1 * | 5/2005 | Edman | ............. 132/76.4 |
| 2007/0214557 A1 | 9/2007 | Qiu | |

* cited by examiner

*Primary Examiner* — Robyn Doan

(57) ABSTRACT

The foot callous removal device has a handle, a cylindrical extension affixed downwardly to the handle, a shoe having a sole, a vamp, and a toe cap connected to the vamp and the sole, an abrasive disposed within the toe cap, a notched receiver disposed laterally and rearwardly within the sole, a collar, the cylindrical extension downwardly affixed within the collar, a lateral projection disposed radialy outward on the collar, a flared end disposed outwardly on the lateral projection, whereby the collar is affixed within the notched receiver of the sole, and the cylindrical extension and handle are substantially perpendicular to the shoe sole.

5 Claims, 4 Drawing Sheets

FOOT CALLOUS REMOVAL DEVICE

CROSS-REFERENCE TO RELATED APPLICATIONS

Not Applicable

FEDERALLY SPONSORED RESEARCH OR DEVELOPMENT

Not Applicable

INCORPORATION BY REFERENCE OF MATERIAL SUBMITTED ON A COMPACT DISK

Not Applicable

To all Whom it May Concern

Be it known that we, Nellie J. Fritts and Carl Lee Helton, citizens of the United States, have invented new and useful improvements in a foot callous removal device as described in this specification.

BACKGROUND OF THE INVENTION

Various instruments have been proposed for foot callous removal. Most such devices require a user to either bend down or to raise their foot, then use a hand held device of some kind to abrade callous for removal. Such devices typically require that a user separately address each area of the foot. This procedure requires considerable time and is also often difficult if not impossible for many people. Those with health issues such as physical challenges often simply cannot perform such tasks. The present device allows a user to abrade any part of the full frontal area of the foot, whether standing or sitting, without having to bend down or raise the foot in any way.

FIELD OF THE INVENTION

The foot callous removal device relates to foot callous removal devices.

SUMMARY OF THE INVENTION

The general purpose of the foot callous removal device, described subsequently in greater detail, is to provide a foot callous removal device which has many novel features that result in an improved foot callous removal device which is not anticipated, rendered obvious, suggested, or even implied by prior art, either alone or in combination thereof.

To attain this, the foot callous removal device provides for a user to abrade callous from feet. Importantly, the shoe has a sole, vamp, and toe cap but no heel. The user can thereby slide the foot into and out of the shoe as needed. The toe cap, importantly, may be entirely interiorly covered with abrasive. The abrasive may be comprised of various materials to best affect callous debridement. A user can bias foot pressure as desired to accomplish desired debridement of callous.

The device may be provided with a set handle and extension length. The device may also be provided with adjustability wherein handle to shoe distance is user determined. Either provides the important stability feature wherein a user easily stabilizes the shoe as needed. With adjustable handle to shoe distance, the first cylindrical extension may be used to engage the second collar that is attached to the shoe sole. The arrangement allows a user to typically be in a seated position, for example, and to grasp the handle close to knee height, perhaps. Choosing to use both extensions might, for example, allow a user to stand while using the device. Standing or seated positions are totally user choice, as is overall distance of handle from the shoe. Additional cylindrical extensions with collars are provided for even further overall handle height determination.

Thus has been broadly outlined the more important features of the improved foot callous removal device so that the detailed description thereof that follows may be better understood and in order that the present contribution to the art may be better appreciated.

An object of the foot callous removal device is to remove callous from feet.

Another object of the foot callous removal device is to remove callous from feet without requiring a user to bend.

A further object of the foot callous removal device is to remove foot callous without requiring a user to elevate a foot.

An added object of the foot callous removal device is to remove foot callous around the entire front portion of the foot.

And, an object of the foot callous removal device is to allow easy foot insertion and removal.

These together with additional objects, features and advantages of the improved foot callous removal device will be readily apparent to those of ordinary skill in the art upon reading the following detailed description of presently preferred, but nonetheless illustrative, embodiments of the improved foot callous removal device when taken in conjunction with the accompanying drawings.

DETAILED DESCRIPTION OF THE DRAWINGS

With reference now to the drawings, and in particular FIGS. 1 through 6 thereof, the principles and concepts of the foot callous removal device generally designated by the reference number 10 will be described.

Figure 1:
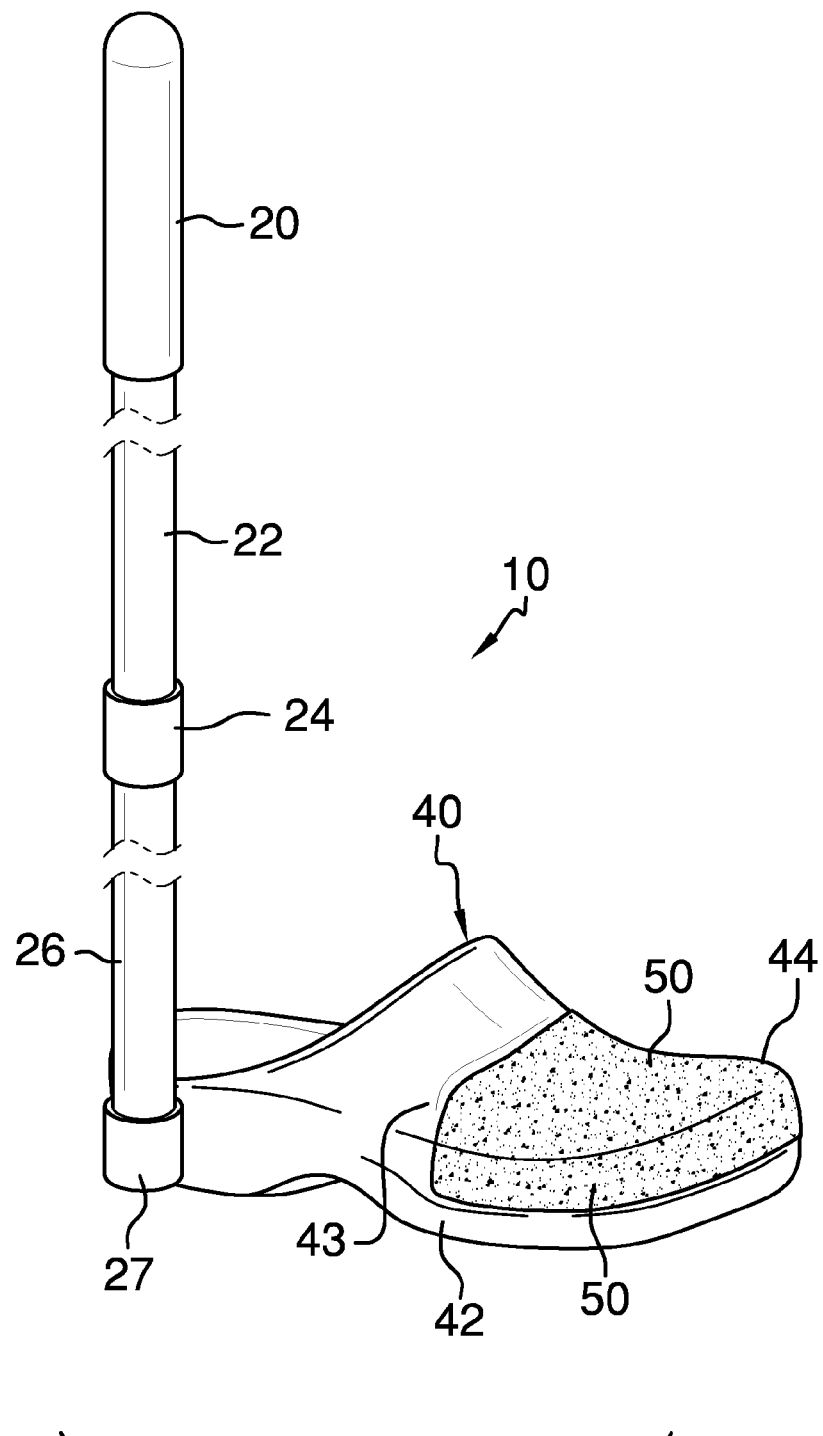
FIG. 1 is a perspective view.

Referring to FIG. 1, the device 10 partially comprises a handle 20.

Figure 2:
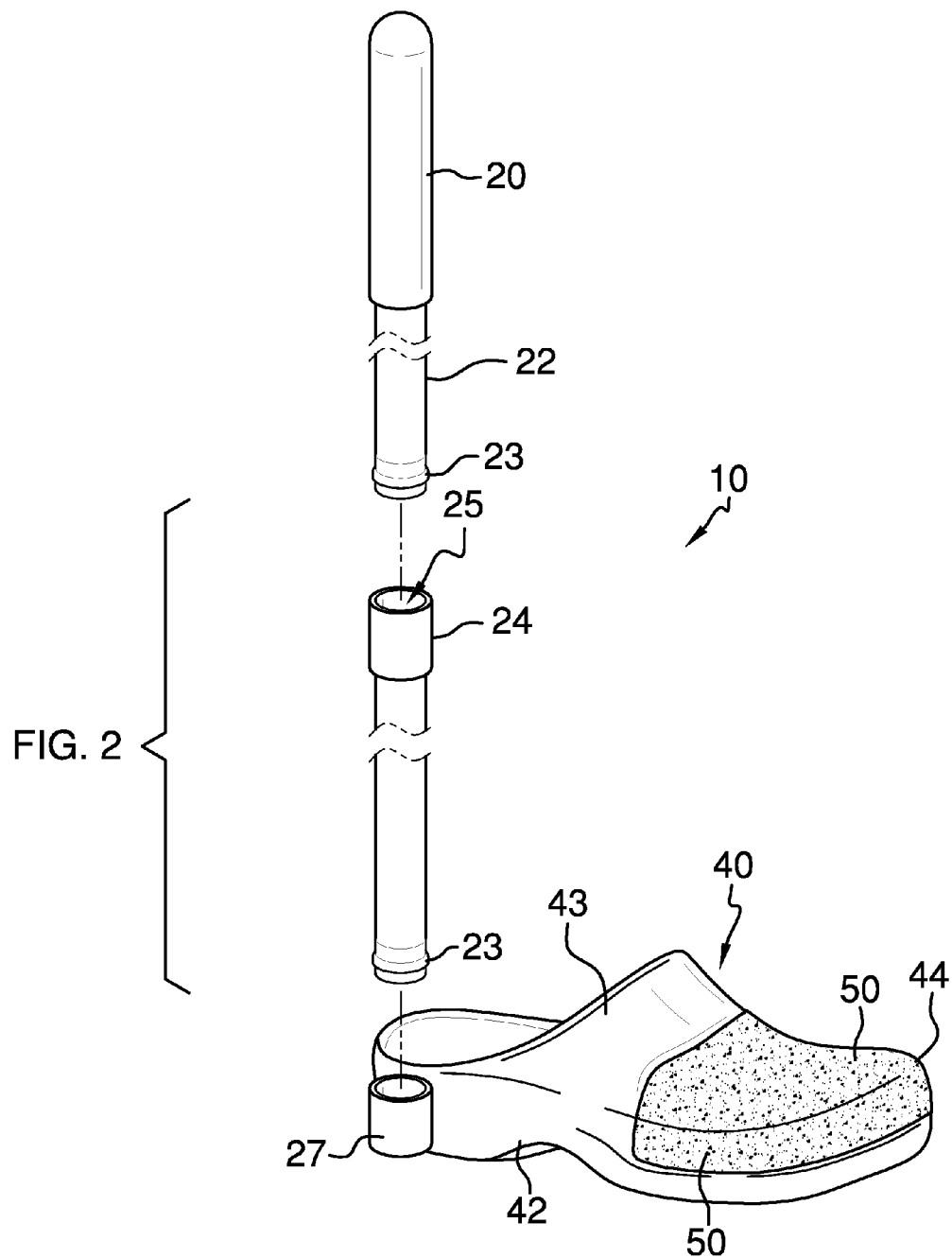
FIG. 2 is an exploded perspective view.

Referring to FIG. 2, the device 10 further comprises a first cylindrical extension 22 affixed downwardly to the handle 20. The circular extrusion 23 downwardly encircles the first cylindrical extension 22. The second cylindrical extension 26 has a first collar 24 disposed upwardly on the second cylindrical extension 26. A collar indent 25 is disposed within the first collar 24, whereby the first cylindrical extension 26 with circular extrusion 23 is removably disposed within the first collar 24. A circular extrusion 23 is disposed downwardly on the second cylindrical extension 26.

Figure 3:
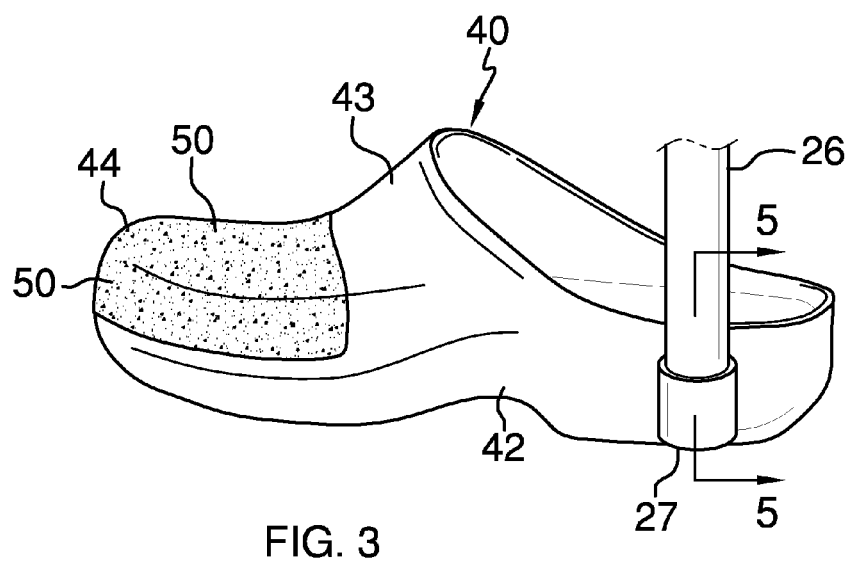
FIG. 3 is a partial lateral perspective view.
Figure 4:
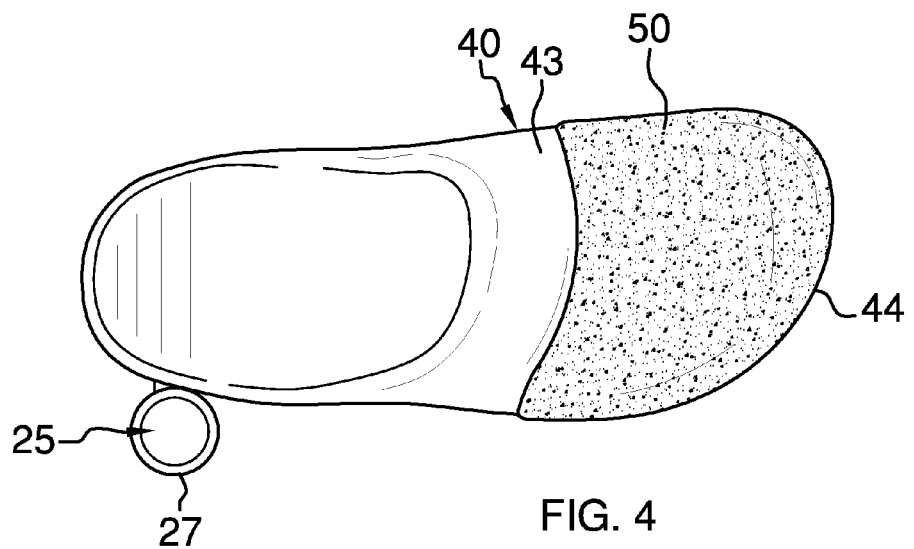
FIG. 4 is a partial top plan view.

Referring to FIG. 3, the device further comprises a shoe 40 having a sole 42, a vamp 43 connected to the sole 42, and a toe cap 44 connected to the vamp 43 and to the sole 42.

Referring to FIG. 4 and again to FIG. 3, an abrasive 50 is disposed fully within the toe cap 44.

Figure 5:
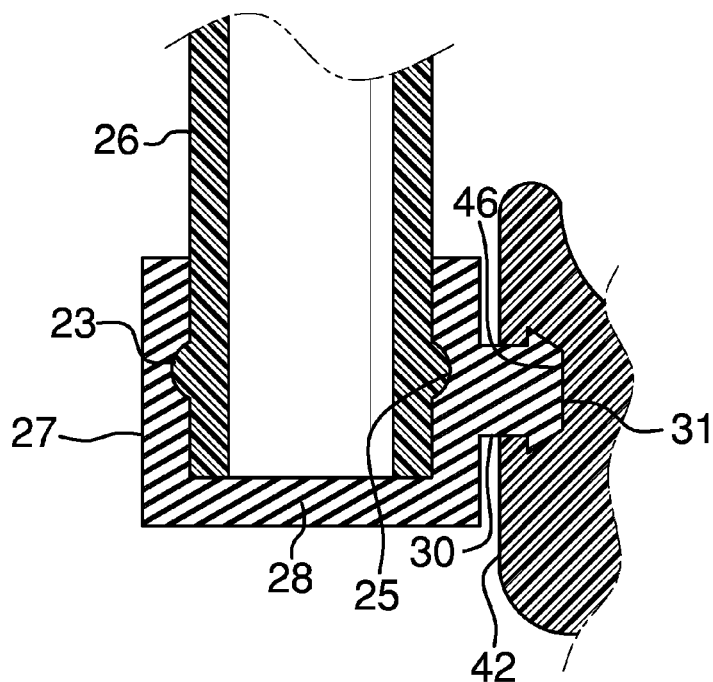
FIG. 5 is a partial cross sectional view of FIG. 3, taken along the line 5-5.

Referring to FIG. 5, the notched receiver 46 is disposed laterally and rearwardly within the sole 42. A collar indent 25 is disposed within the second collar 27. A bottom 28 is disposed within the second collar 27. A lateral projection 30 is disposed radialy outward on the second collar 27. The flared end 31 is disposed outwardly on the lateral projection 30, whereby the second collar 27 is affixed within the notched receiver 46 of the sole 42. The cylindrical extension 26 and handle 20 are substantially perpendicular to the shoe 40 sole 42.

Figure 6:
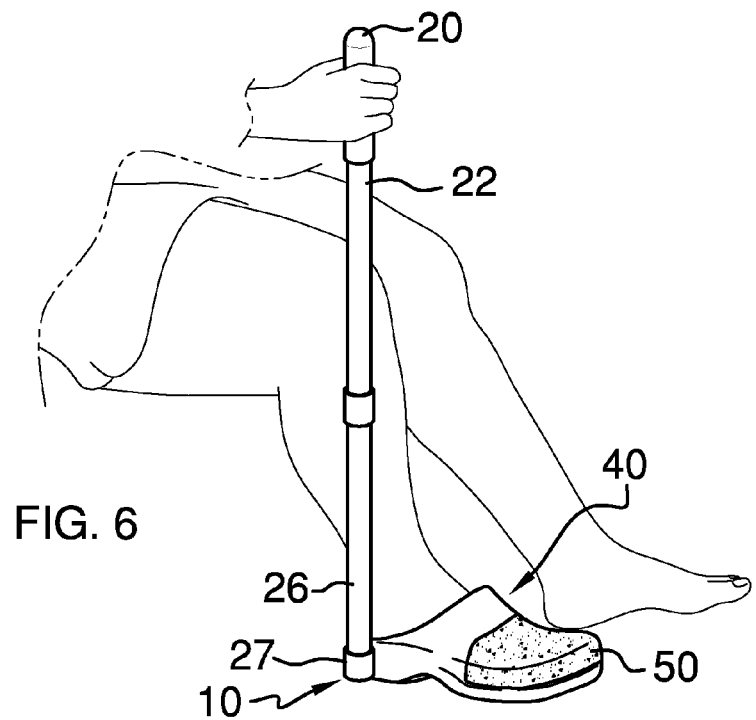
FIG. 6 is a perspective view in use.

Referring to FIG. 6, the user has chosen to sit. The user grasps the handle 20 for stabilizing the device 10. The user is then free to slide their foot and move their foot as desired within the shoe 40. The abrasive 50 within the entire toe cap 44 can thereby abrade callous from the user's foot. The user can bias their foot pressure and movement as desired to focus more on different areas of the foot.

Directional terms such as "front", "back", "in", "out", "downward", "upper", "lower", and the like may have been used in the description. These terms are applicable to the embodiments shown and described in conjunction with the drawings. These terms are merely used for the purpose of description in connection with the drawings and do not necessarily apply to the position in which the foot callous removal device may be used.

What is claimed is:

1. A foot callous removal device comprising, in combination:
   a handle;
   a cylindrical extension affixed downwardly to the handle;
   a shoe having a sole;
   a vamp connected to the sole;
   a toe cap connected to the vamp and the sole;
   an abrasive disposed within the toe cap;
   a notched receiver disposed laterally and rearwardly within the sole;
   a collar, the cylindrical extension downwardly affixed within the collar;
   a lateral projection disposed radialy outward on the collar;
   a flared end disposed outwardly on the lateral projection;
   whereby the collar is affixed within the notched receiver of the sole, the cylindrical extension and handle substantially perpendicular to the shoe sole.

2. The device according to claim 1 wherein the abrasive is disposed fully within the toe cap.

3. The device according to claim 1 wherein the cylindrical extension is removably affixed to the collar.

4. The device according to claim 2 wherein the cylindrical extension is removably affixed to the collar.

5. A foot callous removal device comprising, in combination:
   a handle;
   a first cylindrical extension affixed downwardly to the handle;
   a circular extrusion downwardly encircling the first cylindrical extension;
   a second cylindrical extension;
   a first collar disposed upwardly on the second cylindrical extension;
   a collar indent disposed within the first collar, whereby the first cylindrical extension with circular extrusion is removably disposed within the first collar;
   a circular extrusion disposed downwardly on the second cylindrical extension;
   a shoe having a sole;
   a vamp connected to the sole;
   a toe cap connected to the vamp and the sole;
   an abrasive disposed fully within the toe cap;
   a notched receiver disposed laterally and rearwardly within the sole;
   a second collar;
   a collar indent disposed within the second collar;
   a bottom disposed within the second collar;
   a lateral projection disposed radialy outward on the second collar;
   a flared end disposed outwardly on the lateral projection;
   whereby the second collar is affixed within the notched receiver of the sole, the cylindrical extension and handle substantially perpendicular to the shoe sole.

* * * * *